(12) United States Patent
Jansen et al.

(10) Patent No.: US 8,497,367 B2
(45) Date of Patent: Jul. 30, 2013

(54) SUCRALOSE PURIFICATION PROCESS (75) Inventors: Robert Jansen, Portella LRS (PT);
Gordon Walker, Goring Heath (GB);
John Kerr, South Croydon (GB);
Anthony Baiada, Dagenham (GB)

(73) Assignee: Tate & Lyle Technology Limited, London (GB)

( * ) Notice: Subject to any disclaimer, the term of this patent is extended or adjusted under 35 U.S.C. 154(b) by 687 days.

(21) Appl. No.: 12/413,955

(22) Filed: Mar. 30, 2009

(65) Prior Publication Data
US 2009/0299054 A1 Dec. 3, 2009

Related U.S. Application Data (60) Provisional application No. 61/042,068, filed on Apr. 3, 2008.

(51) Int. Cl.
*C07H 5/02* (2006.01)
(52) U.S. Cl.
USPC .......................................................... 536/124
(58) Field of Classification Search
USPC .......................................................... 536/124
See application file for complete search history.

(56) References Cited

U.S. PATENT DOCUMENTS

| | | | |
|---|---|---|---|
| 4,362,869 A | 12/1982 | Jenner et al. | |
| 4,380,476 A | 4/1983 | Mufti et al. | |
| 4,405,654 A | 9/1983 | Lee | |
| 4,783,526 A | 11/1988 | O'Brien et al. | |
| 4,826,962 A | 5/1989 | Rathbone et al. | |
| 4,889,928 A | 12/1989 | Simpson | |
| 4,950,746 A | 8/1990 | Navia | |
| 4,980,463 A | 12/1990 | Walkup et al. | |
| 5,023,329 A | 6/1991 | Neiditch et al. | |
| 5,034,551 A | 7/1991 | Vernon et al. | |
| 5,089,608 A | 2/1992 | Walkup et al. | |
| 5,128,248 A | 7/1992 | Dordick et al. | |
| 5,141,860 A | 8/1992 | Bornemann et al. | |
| 5,270,071 A | 12/1993 | Sharp et al. | |
| 5,272,137 A | 12/1993 | Blase et al. | |
| 5,298,611 A | 3/1994 | Navia et al. | |
| 5,354,902 A | 10/1994 | Merciadez et al. | |
| 5,374,659 A | 12/1994 | Gowan | |
| 5,384,311 A | 1/1995 | Antenucci et al. | |
| 5,397,588 A | 3/1995 | Antenucci et al. | |
| 5,409,907 A | 4/1995 | Blase et al. | |
| 5,426,220 A | 6/1995 | Baniel | |
| 5,440,026 A | 8/1995 | Khan et al. | |
| 5,470,969 A | 11/1995 | Sankey et al. | |
| 5,498,709 A * | 3/1996 | Navia et al. ............ 536/124 | |
| 5,530,106 A * | 6/1996 | Navia et al. ............ 536/4.1 | |
| 5,593,696 A | 1/1997 | McNally et al. | |
| 5,621,005 A | 4/1997 | Gowan | |
| 5,658,919 A | 8/1997 | Ratnaraj et al. | |
| 5,674,522 A | 10/1997 | Shah et al. | |
| 5,817,340 A | 10/1998 | Roche et al. | |
| 5,876,759 A | 3/1999 | Gowan | |
| 5,977,349 A | 11/1999 | Catani et al. | |
| 6,080,481 A | 6/2000 | Ochs et al. | |
| 6,090,401 A | 7/2000 | Gowan et al. | |
| 6,211,246 B1 | 4/2001 | Gelotte et al. | |
| 6,258,381 B1 | 7/2001 | Luber et al. | |
| 6,265,012 B1 | 7/2001 | Shamil | |
| 6,277,409 B1 | 8/2001 | Luber et al. | |
| 6,646,121 B2 | 11/2003 | El Kabbani et al. | |
| 6,723,877 B1 | 4/2004 | Maliszewskyj | |
| 6,809,198 B2 | 10/2004 | El Kabbani et al. | |
| 6,890,581 B2 | 5/2005 | Vernon et al. | |
| 6,939,962 B2 | 9/2005 | Clark et al. | |
| 6,943,248 B2 | 9/2005 | Catani et al. | |
| 6,998,144 B2 | 2/2006 | Merkel et al. | |
| 6,998,480 B2 | 2/2006 | Catani et al. | |
| 7,049,435 B2 | 5/2006 | Catani et al. | |
| 2002/0157937 A1 | 10/2002 | Cockrem | |
| 2004/0030124 A1 | 2/2004 | Catani et al. | |
| 2006/0149084 A1 | 7/2006 | Domschke | |
| 2006/0188629 A1 | 8/2006 | Liesen et al. | |
| 2006/0205936 A1 | 9/2006 | Jia et al. | |
| 2006/0276639 A1 | 12/2006 | Fry | |
| 2007/0015916 A1 | 1/2007 | El Kabbani et al. | |
| 2007/0100139 A1 | 5/2007 | Fry | |
| 2007/0160732 A1 | 7/2007 | Deshpande et al. | |

(Continued)

FOREIGN PATENT DOCUMENTS

| | | |
|---|---|---|
| DE | 10260085 | 7/2004 |
| EP | 0043649 | 1/1982 |
| EP | 0409549 | 1/1991 |
| EP | 0708110 | 4/1996 |
| GB | 1426018 | 2/1976 |
| WO | 0014052 | 3/2000 |
| WO | 02074403 | 9/2002 |
| WO | WO 03/076453 | 9/2003 |
| WO | WO 03/076454 | 9/2003 |
| WO | WO 2005/090374 | 9/2005 |
| WO | WO 2005/090376 | 9/2005 |
| WO | WO 2006/061855 | 6/2006 |
| WO | WO 2006/061855 A2 * | 6/2006 |
| WO | WO 2006/130169 | 12/2006 |
| WO | WO 2007/017899 | 2/2007 |

(Continued)

OTHER PUBLICATIONS

Bardili, Burkhart, International Search Report and Written Opinion mailed Aug. 24, 2009, 7 pgs.

(Continued)

*Primary Examiner* — Shaojia Anna Jiang
*Assistant Examiner* — Ganapathy Krishnan
(74) *Attorney, Agent, or Firm* — RatnerPrestia (57) ABSTRACT

A process for the extraction of sucralose from an aqueous solution containing at least sucralose, other chlorinated saccharides, sodium chloride and dimethylammonium chloride into an organic solvent for sucralose by contacting said organic solvent with said solution to extract sucralose into the organic solvent. The ratio of sodium chloride to dimethylammonium chloride in the aqueous solution is increased prior to or during contact so as to increase the partition coefficient of sucralose into said organic solvent.

56 Claims, 1 Drawing Sheet

U.S. PATENT DOCUMENTS

2007/0227897 A1 10/2007 Li et al.
2007/0270583 A1 11/2007 Ratnam et al.
2008/0227971 A1 9/2008 Leinhos

FOREIGN PATENT DOCUMENTS

| WO | WO 2007/023505 | 3/2007 |
| WO | WO 2007/052304 | 5/2007 |
| WO | 2008004246 | 1/2008 |
| WO | WO 2008/091539 | 7/2008 |

OTHER PUBLICATIONS

Grand, Dr. Simon; Combined Search and Examination Report; Dec. 17, 2008; 6 pp; South Wales.
DeSilva, F., Water Quality Products, 2006, 11(4), pp. 1-3.
Ault, A.. Techniques and Experiments for Organic Chemistry, 1987, pp. 43-44.
Chen et al., Ind. Engg. Chem. Res., 1999, 38, 1605-1610.
Grant et al, Chemical Dictionary, 1987, p. 122.
Merck Index, 1996, p. 549.
Qin, Y. et al., "Pervaporation Membranes That Are Highly Selective for Acetic Acid over Water," Ind. Eng. Chem. Res., 2003, 42, 582-595.
Schierbaum, Burkhard, et al.; "Isolation of Carboxylic Acids From Aqueous Solutions by Extraction with Dialkylcarboxylic Amides/ Trialkylamines"; Chem. Eng. Technol.; 1999; pp. 37-41; vol. 22; US.
Smith et al, Food Additives Databook, 2003, p. 988.
The Free Dictionary, McGraw- Hill, 2003, pp. 1-2.

* cited by examiner

US 8,497,367 B2

SUCRALOSE PURIFICATION PROCESS

CROSS REFERENCE TO RELATED APPLICATIONS

This application claims priority benefit of U.S. Provisional Appln. No. 61/042,068, filed Apr. 3, 2008, the entirety of which is incorporated herein by reference.

FIELD OF THE INVENTION

The present invention relates to an improvement in the sucralose purification process, especially to one stage thereof, and provides sucralose when so purified.

BACKGROUND TO THE INVENTION

Sucralose, 4,1',6'-trichloro-4,1',6'-trideoxygalactosucrose, a sweetener with a sweetness intensity several hundred times that of sucrose, is derived from sucrose by replacing the hydroxyl groups in the 4, 1', and 6' positions with chlorine. Synthesis of sucralose is technically challenging because of the need to selectively replace specific hydroxyl groups with chlorine atoms, while preserving other hydroxyl groups including a highly reactive primary hydroxyl group. Numerous approaches to this synthesis have been developed. See, e.g., U.S. Pat. Nos. 4,362,869; 4,826,962; 4,980,463; and 5,141,860, which are expressly incorporated by reference herein. However, such approaches typically provide a product that contains varying levels of other chlorinated sugar compounds in addition to sucralose. Increasingly, efforts have been directed toward the isolation of sucralose in highly pure form from this complex mixture of related chlorinated materials. Early reported work typically involved crystallizing sucralose directly from the synthesis mixture, a process that yields a material with high impurity levels. Sucralose is sometimes purified from a synthesis mixture by silica gel chromatography. See, e.g., U.S. Pat. No. 5,128,248, which is expressly incorporated by reference herein. That procedure, due to its use of silica gel, may be ill-suited to large-volume commercial production of highly pure sucralose. In addition, relatively little attention has been focused on other approaches for removing chlorinated sugar impurities from sucralose. Efficient removal of these impurities is important because, even at quite low concentrations, they can have an adverse impact on the sweetness, taste, and flavor-modifying properties of sucralose.

The synthesis of sucralose typically results in the concomitant synthesis of a range of chlorinated sucrose moieties which need to be separated and removed from the target molecule (sucralose) during the manufacturing process. Typically, after preparation, the sucralose containing feed stream is subjected to a number of purification steps, of which solvent extraction is one purification process typically employed for the removal of species less and more hydrophobic than sucralose itself.

Various methods for the synthesis of sucralose and related compounds have been suggested. U.S. Pat. No. 4,405,654, which is expressly incorporated by reference herein, for example, relates to a process for the synthesis of a related compound, 1',4',6'-trichloro-1',4',6'-trideoxysucrose. After the deacetylation of a pentaacetate precursor, the reaction mixture is purified by column chromatography on silica gel. The product is eluted from the silica gel with ethyl acetate.

U.S. Pat. No. 4,980,463, which is expressly incorporated by reference herein, relates to a process in which sucralose is produced by KOH treatment of a methanol solution of sucralose-6-benzoate. The methanol is removed by evaporation, and the residue is dissolved in water. The aqueous solution is extracted three times with separate one-quarter volumes of ethyl acetate. The combined organic extracts are concentrated and then back extracted with water to recover sucralose present in the ethyl acetate. The combined aqueous portions are concentrated and treated with a decolorizing agent. Additional concentration permits crystallization of the sucralose. The recovered crystals have a reported purity of 99.6%. Purification to this level is achieved primarily through crystallization, rather than by solvent extraction processes. It is noteworthy that this approach only involves ethyl acetate extraction of the original aqueous solution, and sucralose is never re-extracted from the aqueous solution into an organic phase, thereby achieving a further purification.

U.S. Pat. No. 5,034,551, which is expressly incorporated by reference herein, relates to a similar process in which a base is used to hydrolyze a solution of sucralose-6-benzoate in methanol. The methanol is removed by evaporation, and the sucralose-containing residue is dissolved in water. This solution is extracted three times with separate one-quarter volumes of ethyl acetate. The remaining aqueous layer is decolorized with charcoal and concentrated, and the sucralose is allowed to crystallize.

U.S. Pat. No. 5,498,709, which is expressly incorporated by reference herein, relates to solvents that may be used to extract sucralose from the aqueous brine produced by alkaline hydrolysis of a 6-acyl ester precursor compound. Possible solvents include methyl acetate, ethyl acetate, methyl ethyl ketone, methyl isobutyl ketone, methyl isoamyl ketone, methylene chloride, chloroform, diethyl ether, and methyl tertiary butyl ether. Ethyl acetate is presented as a suitable solvent for reasons of extraction selectivity, ease of recycling, and toxicological safety.

U.S. Pat. No. 5,498,709 also relates to a process in which the aqueous solution remaining after ester hydrolysis of sucralose precursors is concentrated and then sucralose is isolated by three sequential extractions with ethyl acetate or other suitable solvent. The extracts may then be combined, and optionally washed with water to remove any dimethylformamide remaining prior to recovering the sucralose by concentration and crystallization. This patent also relates to processes in which sucralose contained in the aqueous brine obtained after alkaline deesterification is extracted into a solvent not miscible with brine, such as dichloromethane, chloroform, 2-butanone, cyclohexanone, or ethyl acetate. The organic extracts may then be back extracted with water to transfer the sucralose back into the aqueous phase. This aqueous solution may then be decolorized and concentrated, and the resulting purified sucralose is recovered by crystallization. This approach yields a relatively impure material.

An additional approach discussed within U.S. Pat. No. 5,498,709 involves the toluene extraction of the alkaline solution remaining after deesterification. Specifically, the solution is extracted twice with toluene to remove non-polar impurities. The aqueous solution is then extracted repeatedly with 2-butanone. The 2-butanone extracts are combined, and the solvent is evaporated to yield a reddish syrup containing sucralose.

U.S. Pat. No. 5,530,106, which is expressly incorporated by reference herein, relates to an extractive process for a crude sucralose solution obtained after alkaline hydrolysis of sucralose-6-acetate and subsequent neutralization. The aqueous sucralose solution is extracted with water saturated ethyl acetate. Some impurities are selectively partitioned to the organic phase by this extraction. Subsequently, the ethyl acetate phase is backwashed with water in order to recover a portion of the sucralose that had also partitioned into the organic phase. The aqueous solution and the aqueous backwash are combined, concentrated and decolorized, and the sucralose is recovered by crystallization from the aqueous phase.

U.S. Pat. No. 7,049,435, which is expressly incorporated by reference herein, relates to methods for removing impurities from a composition comprising sucralose and impurities in a first solvent comprising the steps of performing a liquid extraction of the composition with a second immiscible solvent to effect removal of the impurities into the second solvent and performing a second extraction of the composition with a third immiscible solvent to effect the transfer of the sucralose into the third solvent and the retention of the impurities in the first solvent.

SUMMARY OF THE INVENTION

The present invention provides an improvement in the solvent extraction of sucralose or a sucralose-6-acylate from an aqueous solution containing it. In carrying out this solvent extraction, we have observed that the partition coefficient of the sucralose or sucralose-6-acylate between the aqueous solution and the extraction solvent is relatively unfavorable and have now surprisingly discovered that this is due to the presence of dimethylammonium chloride (DMAHCl) and that the effect may be ameliorated by increasing the ratio of NaCl to DMAHCl.

Thus, by controlling the amounts of NaCl and DMAHCl and their ratios, it is possible to affect the distribution coefficient of sucralose (and other chlorinated species) into the organic phase. Furthermore, it has been found that the exact value of the distribution coefficient (K) is a function of the wt % NaCl, the wt % DMAHCl and their relative amounts. This fact can be used to control the value of k by varying the amounts of these salts dissolved in the aqueous phase. Specifically, by increasing the ratio of sodium chloride to DMAHCl, extraction of sucralose or sucralose-6-acylate into the organic phase can be enhanced.

Thus, one embodiment of the invention relates to a process for the extraction of sucralose or a sucralose-6-acylate from an aqueous solution containing at least said sucralose or said sucralose-6-acylate, other chlorinated saccharides, dimethylammonium chloride, and a further chloride selected from the group consisting of alkali metal chlorides, ammonium chloride and alkaline earth metal chlorides, into an organic solvent for said sucralose or said sucralose-6-acylate by contacting said organic solvent with said solution to extract said sucralose or said sucralose-6-acylate into the organic solvent, in which the ratio of said further chloride to dimethylammonium chloride in said aqueous solution is increased prior to or during said contact so as to increase the partition coefficient of said sucralose or said sucralose-6-acylate into said organic solvent.

Another embodiment of the present invention relates to a process for the purification of sucralose from a feed stream from the synthesis of sucralose, in which the feed stream is subjected to a series of purification steps, at least one of the steps comprising: extracting sucralose from an aqueous solution containing at least sucralose, other chlorinated saccharides, dimethylammonium chloride, and a further chloride selected from the group consisting of alkali metal chlorides, ammonium chloride and alkaline earth metal chlorides, into an organic solvent for sucralose by contacting said organic solvent with said solution to extract sucralose into the organic solvent, in which the ratio of said further chloride to dimethylammonium chloride in said aqueous solution is increased prior to or during said contact so as to increase the partition coefficient of sucralose into said organic solvent.

In a further embodiment of the present invention, there is provided a process for the production of sucralose from a feed stream from the synthesis of sucralose-6-acylate, in which the feed stream is subjected to a series of purification steps and the purified sucralose-6-acylate is then deacylated to give sucralose, at least one of the purification steps comprising: extracting sucralose-6-acylate from an aqueous solution containing at least sucralose-6-acylate, other chlorinated saccharides, dimethylammonium chloride, and a further chloride selected from the group consisting of alkali metal chlorides, ammonium chloride and alkaline earth metal chlorides, into an organic solvent for sucralose-6-acylate by contacting said organic solvent with said solution to extract sucralose-6-acylate into the organic solvent, in which the ratio of said further chloride to dimethylammonium chloride in said aqueous solution is increased prior to or during said contact so as to increase the partition coefficient of sucralose-6-acylate into said organic solvent.

In yet another embodiment, the invention provides a process for the extraction of sucralose or sucralose-6-acylate from an aqueous solution containing at least said sucralose or said sucralose-6-acylate, other chlorinated saccharides, dimethylammonium chloride, and a further chloride selected from the group consisting of alkali metal chlorides, ammonium chloride and alkaline earth metal chlorides, into an organic solvent for said sucralose or said sucralose-6-acylate, which comprises the steps:

removing dimethylammonium chloride from the aqueous solution to increase the ratio of said further chloride to dimethylammonium chloride and thus increase the partition coefficient of sucralose into said organic solvent; and contacting said organic solvent with the resulting solution to extract said sucralose or said sucralose-6-acylate into the organic solvent.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, pH, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a solvent" is a reference to one or more solvents, and may include appropriate mixtures of solvents, and includes equivalents thereof known to those skilled in the art and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Definitions

"Aromatic": as used herein includes compounds containing cyclic structures with resonant conjugated double bonds such as, for example, benzene, toluene, or xylene.

"Backwash": as used herein includes an extractive step in which a second solvent phase remaining after its use to extract a first solvent is re-extracted with a small portion of the first solvent. This provides a means for recovering valuable materials such as sucralose or other species that have partially partitioned into the second solvent which may be employed to semiselectively remove impurities. The backwash solution may be combined with the first solvent, so that the recovery of the valuable product such as sucralose or other species may be maximized in the first solvent. The backwash solution optionally may be concentrated prior to its addition to the first solvent.

"Crystallization": as used herein includes processes in which crystals are obtained from a solution. The initiation of crystal formation may be spontaneous, or it may require the addition of seed crystals. As used herein, "crystallization" also describes the situation in which a solid or liquid material is dissolved in a solvent to yield a solution which is then rendered saturated or supersaturated so as to obtain crystals. Also, included in the term "crystallization" are the ancillary processes of filtering or centrifuging the crystals, dewatering the crystals, washing the crystals with one or more solvents, drying the crystals, and harvesting the final product so obtained.

"Feed mixture": as used herein includes any mixture of compounds that results from any synthetic process for sucralose. Includes mixtures of sucralose and any and all impurities.

"Impurity": as used herein includes compounds other than sucralose and includes products of any number of processes for synthesizing sucralose that are not sucralose. "Impurity" includes any monochloro-, dichloro-, tetrachloro-, and pentachloro-derivative of sucrose and any other disaccharide or trisaccharide derived from sucrose, sucralose, or their constituent monosaccharides, as well as any trichloro-derivative other than sucralose itself, whether present in free form or as esters of carboxylic acids. "Impurity" includes any of the halogenated sugar derivatives, such as dichlorosucrose acetate, 6,1',6'-trichlorosucrose, 4,6,6'-trichlorosucrose, 4,1',4',6'-tetrachlorogalactotagatose, 4,1',6'-trichlorogalactosucrose-6-acetate, 4,6,1',6'-tetrachlorogalactosucrose, 4,1'-dichlorogalactosucrose, 3',6'-dichloroanhydrosucrose, 4,6'-dichlorogalactosucrose, 1',6'-dichlorosucrose, 6,6'-dichlorosucrose, 4,1',6'-trichlorosucrose, 4,6,6'-trichlorogalactosucrose, 4,1',5'-trichlorogalactosucrose-6-acetate, and 4,6,6'-trichlorogalactosucrose. "Impurity" includes any organic or inorganic salt, carbohydrate, or acylated carbohydrate, other than sucralose-6-acylate.

"Solvent": as used herein includes a liquid that can dissolve or substantially disperse another substance.

Process

EP 0409549 discloses a process for the chlorination of a sucrose-6-acylate in a tertiary amide reaction vehicle to produce a sucralose-6-acylate, such as sucralose-6-acetate. A large excess of a chlorination agent, such as phosgene, is used in this process. Following the chlorination reaction, the excess chlorination agent is quenched using a suitable base, thereby forming the chloride salt of the base. At this stage, where the reaction solvent is, as seems usual, dimethylformamide, some of the solvent also may react with the base to produce dimethylammonium chloride. The resulting product stream thus comprises a sucralose-6-acylate, the tertiary amide reaction vehicle, water, and salts. The sucralose-6-acylate is then deacylated to give sucralose. At some stage, before or after this deacylation, the reaction mixture is purified, with the aim of reducing the content of salts and DMAHCl. Where the deacylation is carried out, as it may be, in dimethylformamide, this deacylation step may also result in the formation of DMAHCl.

Where, as is common, the base used is sodium hydroxide, the salt formed is sodium chloride. However, other bases may be used, for example other alkali metal hydroxides, alkaline earth metal hydroxides or ammonium hydroxide, so that the salt is an alkali metal chloride, an alkaline earth metal chloride or ammonium chloride.

The aqueous feed solution which is the starting material for the process of the present invention thus contains, in addition to sucralose or sucralose-6-acylate, various impurities derived from side reactions, sodium or another chloride and dimethylammonium chloride. Depending upon the procedures to which the feed solution has already been subjected, greater or lesser adjustments may be needed to the NaCl:DMAHCl ratio. Since it is necessary to increase this ratio, this may be achieved either by adding more of the sodium or other chloride or by removing dimethylammonium chloride. Ultimately, it will be necessary to remove anything added, and so the preferred option is to remove dimethylammonium chloride. This may be achieved by a variety of methods well known to those skilled in the art.

For example, one useful method of removing the DMAHCl is first to adjust the pH, if necessary, to form free dimethylamine, and then to evaporate off this dimethylamine under vacuum. It has generally been found most convenient to raise the pH to a value of at least 10, and more suitably about 11, to form free DMA from the DMAHCl. A vacuum is then applied to the reaction medium to strip off the DMA—removal of the DMA may be enhanced by raising the temperature to volatilize the DMA.

Another method of removing DMAHCl employs a resin. For example, this may be carried out as follows:

Prepare a strong cation resin, such as DOW HCRS or Purolite C120E, by washing with either 10% NaCl or 5% NaOH. Pack a resin bed in low ionic content water. Prepare a crude aqueous product solution of sucralose, for example by the method disclosed in U.S. Pat. No. 5,498,709, and remove NaCl by evaporation. Greater reductions in salt increase resin capacity for DMA. At least half the salt should be removed. The partially desalted filtrate may be diluted to lower viscosity and enhance flowability. To a column of resin flushed of regenerate, apply sufficient filtrate to apply 1-3 equivalents of DMA. Follow the application with low ion flush to displace the desirable carbohydrate. The resin may be regenerated with either dilute caustic or 8-12% NaCl.

However the DMAHCl is removed, sufficient is preferably removed to reduce its concentration in the feed solution to a value not greater than 20,000 ppm (on sample), more preferably not greater than 1,000 ppm. In any event, by whatever means the NaCl:DMAHCl ratio is altered, it is preferably increased to a value of from 10:1 to 100:1, more preferably from 10:1 to 25:1.

Prior to the extraction step, it is desirable that the aqueous solution should be evaporated, or otherwise treated, to increase the dry solids content, e.g. to a level of from 15% to 65%, more preferably from 30% to 55%.

The choice of solvent is determined by the relative solubilities of sucralose and the principal impurities in the organic solvent and in the aqueous feed stream, as well as such other factors as flammability, ease of recycling within the process, environmental concerns, toxicity, and cost. The organic solvent can be intentionally saturated with water before use in the extraction step. Mixtures of organic solvents can be used. Solvents contemplated for use as the organic solvent include those that are immiscible with water and in which halogenated sucrose derivatives, such as sucralose, are readily soluble. Also included are solvents that are partially soluble in a first solvent such as water, an aqueous solution, or other solvent in which halogenated sucrose derivatives are readily soluble, but in which the second solvent still forms a separate phase when mixed with the first solvent in proper ratios and under proper conditions. Typical organic solvents include, but are not limited to, methyl acetate, ethyl acetate, methyl ethyl ketone, methyl iso-butyl ketone, methyl iso-amyl ketone, methylene chloride, chloroform, diethyl ether, methyl t-butyl ether, n-pentane, n-hexane, n-heptane, n-octane, isooctane, 1,1,1-trichloroethane, n-dodecane, white spirit, turpentine, cyclohexane, propyl acetate, butyl acetate, amyl acetate, carbon tetrachloride, xylene, toluene, benzene, trichloroethylene, 2-butoxyethanol acetate (butyl CELLOSOLVE® acetate), ethylene dichloride, butanol, morpholine, and mixtures thereof. The first organic solvent preferably comprises methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, or n-butanol, either as a single solvent, or as a mixed solvent with these solvents, or with other solvents from the first list. The first solvent more preferably comprises ethyl acetate, iso-propyl acetate, n-propyl acetate, n-butyl acetate, methyl iso-butyl ketone, or n-butanol, either as a single solvent, or as a mixed solvent with these solvents, or with other solvents from the first or second list. Ethyl acetate is the most preferred solvent. Diethyl ether, methyl t-butyl ether, n-pentane, n-hexane, n-heptane, n-octane, isooctane, 1,1,1-trichloroethane, n-dodecane, white spirit, turpentine, cyclohexane, carbon tetrachloride, xylene, toluene, benzene, trichloroethylene, 2-butoxyethanol acetate (butyl CELLOSOLVE® acetate), ethylene dichloride, and morpholine are generally not preferred as single solvents, but may be used in mixed solvents as described.

In the extraction step, the volume ratio of the organic solvent to the aqueous feed solution is commonly from 2:1 to 5:1, more commonly from 3:1 to 4:1, in order to optimize the extraction. The extraction may be carried out by any means known in the art for liquid-liquid extraction.

For example, these include methods of agitation in a standard vessel, followed by settling and decanting, continuous column extractors, and/or continuous mixing and decanting. Batch, continuous and continuous countercurrent equipment can be used in the present invention. Examples of this equipment include, but are not limited to, any Karr reciprocating plate column (Koch Inc., Kansas City, Mo.), any Scheibel Column (Koch Inc., Kansas City, Mo.), any packed column, any pulsed packed column, any bank of mixer-settlers, any bank of mixers and centrifugal separators, and any centrifugal counter current extractors (e.g., extractors manufactured by Robatel Inc., Pittsfield Mass.).

Indeed, a variety of extractive approaches may be advantageously employed in this invention, and the scope of the invention is therefore not intended to be limited to a specific configuration of equipment. Furthermore, the different process steps described herein (first extraction, backwash of the first extraction, and second extraction) may be performed in different vessels or pieces of equipment. Alternatively, all of these steps may be performed in the same vessel or, in certain aspects, in any order or simultaneously.

Where the material to which the present invention is applied is a sucralose-6-acylate, the acylate group may be any such group suitable for protecting the 6-position of sucrose during a chlorination reaction; however, the acetate and benzoate are preferred.

If the process of the present invention is applied to a sucralose-6-acylate, the compound must be deacylated to afford sucralose. Methods for performing the deacylation are well known in the art. For example, the method disclosed in U.S. Pat. No. 6,890,581, incorporated herein in its entirety by reference, can be used.

The sucralose purified according to the method of the present invention can, if desired, by further purified. Suitable techniques include liquid/liquid extraction and crystallization. Suitable techniques are disclosed in U.S. Pat. Nos. 7,049,435 and 6,998,480, both of which are incorporated herein in their entirety by reference.

Preparation of Sucrose-6-Ester

Selective protection of the 6-hydroxyl of sucrose can be carried out by reaction of sucrose with a carboxylic acid anhydride, such as acetic anhydride or benzoic anhydride, in an anhydrous polar aprotic solvent in the presence of an organotin-based acylation promoter, at a temperature and for a period of time sufficient to produce the sucrose-6-ester. The 6-ester group shields the hydroxyl on the 6 position from the chlorination reaction. Accordingly, any ester group that is stable to the conditions of the chlorination reaction and which can be removed under conditions that do not affect the resulting sucralose can be used. When sucrose-6-acetate is prepared, 1,3-diacetoxy-1,1,3,3-tetrabutyldistannoxane, for example, can be used as the organotin-based acylation promoter and acetic anhydride as the carboxylic acid anhydride. Preparation of sucrose-6-esters is disclosed in, for example, O'Brien, U.S. Pat. No. 4,783,526; Navia, U.S. Pat. No. 4,950,746; Simpson, U.S. Pat. No. 4,889,928; Neiditch, U.S. Pat. No. 5,023,329; Walkup, U.S. Pat. No. 5,089,608; Vernon, U.S. Pat. No. 5,034,551; Sankey, U.S. Pat. No. 5,470,969; Kahn, U.S. Pat. No. 5,440,026; Clark, U.S. Pat. No. 6,939,962, and Li, U.S. Pat. Pub. 2007/0227897 A1; the disclosures of which are all incorporated herein by reference.

Preparation of Sucralose-6-Ester Containing Feed Streams

To convert sucrose-6-ester to sucralose-6-ester, the hydroxyls at the 4, 1', and 6' positions of the sucrose-6-ester are converted to chloro groups, and the stereochemical configuration at the 4 position is inverted. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference.

The chlorination process comprises the following steps. A reaction mixture is prepared comprising the sucrose-6-ester, a tertiary amide, and at least seven molar equivalents of a chlorination agent. For example, in one process, the sucrose-6-ester can be added in a feed stream that comprises about 20 wt % to about 40 wt % of the sucrose-6-ester. The ratio by weight of tertiary amide to total carbohydrate in the reaction mixture may be about 5:1 to about 12:1. Alternatively, a preformed chloroformiminium salt, such as (chloromethylene)dimethylammonium chloride (Arnold's reagent), can be used. (Chloromethylene)dimethylammonium chloride can be prepared, for example, by the reaction of phosgene with N,N-dimethyl formamide. Typically, the molar ratio of the (chloromethylene)dimethylammonium salt to the sucrose-6-ester is about 7:1 to about 11:1.

Subsequently, the hydroxyl groups of the sucrose-6-ester at the 2, 3, 4, 1', 3', 4', and 6' positions are converted to O-alkylformiminium groups. The resulting reaction mixture is heated at a temperature or temperatures and for a period of time or times sufficient to produce a product containing a derivative of sucralose-6-ester in which the remaining hydroxyl groups remain as O-alkylformiminium groups. For example, Walkup, U.S. Pat. No. 4,980,463, the disclosure of which is incorporated herein by reference, and Fry, U.S. 2007/0100139, the disclosure of which is incorporated herein by reference, disclose such processes.

Because formation of a chloroformiminium salt or Vilsmeier reagent is not essential to the chlorination reaction, chlorination agent refers to any compound that can be used to form a chloroformiminium salt or Vilsmeier reagent, or that can convert the hydroxyl groups of a sucrose-6-ester to chloro groups. Some chlorination agents that can be used include, for example, phosgene, phosphorus oxychloride, phosphorus pentachloride, thionyl chloride, sulfuryl chloride, oxalyl chloride, trichloromethyl chloroformate ("diphosgene"), bis(trichloromethyl) carbonate ("triphosgene"), and methane sulfonylchloride. Tertiary amides that can be used include, for example, N,N-dimethyl formamide (DMF), N-formyl piperidine, N-formyl morpholine, and N,N-diethyl formamide. When N,N-dimethyl formamide is used as the tertiary amide, it can also be used as the reaction solvent. Co-solvents can be used at up to about 80 vol % or more of the liquid phase of the reaction medium. Useful co-solvents are those which are both chemically inert and which provide sufficient solvent power to enable the reaction to become essentially homogeneous at the monochlorination stage, for example toluene, o-xylene, 1,1,2-trichloroethane, 1,2-diethoxyethane, diethylene glycol dimethyl ether.

Quenching of the reaction mixture restores the hydroxyl groups at the 2, 3, 3', and 4' positions and forms the sucralose-6-ester. The reaction mixture can be quenched by the addition of about 0.5 to about 2.0 molar equivalents, typically about 1.0 to about 1.5 molar equivalents, of alkali relative to the amount of chlorination agent used in the reaction. An aqueous solution of an alkali metal hydroxide, such as sodium or potassium hydroxide; an aqueous slurry of an alkaline earth metal hydroxide, such as calcium hydroxide; or aqueous ammonium hydroxide can be used to quench the reaction. For example, an aqueous solution of an alkali metal hydroxide, such as aqueous sodium hydroxide, that contains about 5 wt % to about 35 wt %, typically about 8 wt % to about 20 wt %, and preferably about 10 wt % to about 12 wt % can be used.

As described below, quenching can be carried out by addition of alkali to the reaction mixture, by the dual stream process, or by the circulated process. In each case pH and temperature are controlled during addition of the alkali. Quenching is typically carried out at a pH between about 8.5 to about 10.5 and at a temperature of about 0° C. to about 60° C. Preferably, the pH should not be permitted to rise above about 10.5 during the course of the quenching reaction.

In the dual stream process, quenching is carried out by slow addition of the aqueous alkali with simultaneous slow addition of the chlorination reaction material into a reaction vessel. The chlorination reaction mixture and aqueous alkali are simultaneously added slowly until the desired quantity of chlorination reaction mixture has been added. Further aqueous alkali is added until the desired pH is reached. Then the temperature and pH are maintained at the desired levels for the remainder of the reaction. This process can be a batch or continuous process.

In the circulated process, quenching is carried out by circulating the chlorination reaction mixture from a vessel through a circulation loop. Chlorination reaction mixture and aqueous alkali are added slowly into this circulation loop. Sufficient aqueous alkali is added until the desired pH is reached. Then the temperature and pH are maintained at the desired levels for the remainder of the reaction. This process can be a batch or continuous process.

Following quenching, the reaction mixture can be neutralized by the addition of aqueous acid, for example aqueous hydrochloric acid. The resulting mixture comprises sucralose 6-ester, other carbohydrate including chlorinated carbohydrate impurities, unreacted tertiary amide, and salts in an aqueous solvent in which the predominant solvent is water.

Conversion of Sucralose-6-Ester to Sucralose

The sucralose-6-ester containing aqueous feed stream typically comprises both sucralose and sucralose-6-ester. Methods for hydrolyzing sucralose-6-ester are disclosed, for example in Catani, U.S. Pat. Nos. 5,977,349, 6,943,248, 6,998,480, and 7,049,435; Vernon, U.S. Pat. No. 6,890,581; El Kabbani, U.S. Pat. Nos. 6,809,198, and 6,646,121; Navia, U.S. Pat. Nos. 5,298,611 and 5,498,709, and U.S. Pat. Pub. 2004/0030124; Liesen, U.S. Pat. Pub. 2006/0188629 A1; Fry, U.S. Pat. Pub. 2006/0276639 A1; El Kabbani, U.S. Pat. Pub. 2007/0015916 A1; Deshpande, U.S. Pat. Pub. 2007/0160732 A1; and Ratnam, U.S. Pat. Pub. 2007/0270583 A1; the disclosures of which are all incorporated herein by reference.

For example, (a) sucralose-6-ester can be hydrolyzed to sucralose by raising the pH of the reaction mixture to about 11±1 at a temperature and for a time sufficient to effect removal of the protecting group, and (b) the tertiary amide is removed by, for example, steam stripping. Either step (a) or step (b) can be carried first. Alternatively, conversion of sucralose-6-ester to sucralose can be carried in methanol containing sodium methoxide. A trans-esterification reaction occurs that forms sucralose and the methyl ester of the acid, for example methyl acetate when the sucralose-6-ester is sucralose-6-acetate. The methyl ester of the acid can be removed by distillation, and the resulting sucralose containing product dissolved in water.

Industrial Applicability

The process of the invention is useful in the preparation of sucralose. The invention provides an increased yield of crystalline sucralose from a feed of an impure aqueous sucralose solution such as one obtained by alkaline deacylation of a 6-O-acyl precursor and neutralization.

Sucralose is a high-intensity sweetener that can be used in many food and beverage applications, as well as in other applications. Such applications include, for example, beverages, combination sweeteners, consumer products, sweetener products, tablet cores (Luber, U.S. Pat. No. 6,277,409), pharmaceutical compositions (Luber, U.S. Pat. No. 6,258,381; Roche, U.S. Pat. No. 5,817,340; and McNally, U.S. Pat. No. 5,593,696), rapidly absorbed liquid compositions (Gelotte, U.S. Pat. No. 6,211,246), stable foam compositions (Gowan, Jr., U.S. Pat. No. 6,090,401), dental floss (Ochs, U.S. Pat. No. 6,080,481), rapidly disintegrating pharmaceutical dosage forms (Gowan, Jr., U.S. Pat. No. 5,876,759), beverage concentrates for medicinal purposes (Shah, U.S. Pat. No. 5,674,522), aqueous pharmaceutical suspensions (Ratnaraj, U.S. Pat. No. 5,658,919; Gowan, Jr. U.S. Pat. Nos. 5,621,005 and 5,374,659; and Blase, U.S. Pat. Nos. 5,409,907 and 5,272,137), fruit spreads (Antenucci, U.S. Pat. No. 5,397,588; and Sharp, 5,270,071), liquid concentrate compositions (Antenucci, U.S. Pat. No. 5,384,311), and stabilized sorbic acid solutions (Merciadez, U.S. Pat. No. 5,354,902). The determination of an acceptable sweetness can be accomplished by a variety of standard "taste test" protocols known in the art which are well known to those skilled in the art, such as, for example, the protocols referred to in Merkel, U.S. Pat. No. 6,998,144, and Shamil, U.S. Pat. No. 6,265,012.

The invention is further illustrated by reference to the following examples, but it should be recognized that many variations are possible and could be used by a person skilled in the art.

EXAMPLE 1

Removal of Dimethylammonium Chloride

A sucralose solution containing various impurities can be obtained by a number of previously disclosed processes for synthesizing sucralose, as set out above. See, e.g., U.S. Pat. No. 5,498,709. In one embodiment of the present invention, a 6-O-acyl sucralose derivative was deacylated and steam stripped to remove dimethylformamide remaining from the chlorination reaction. This resulted in an aqueous solution with approximately the following composition:

5% total carbohydrate, of which 25% were dichlorosaccharides, 5% were tetrachlorosaccharides, 5% were other trichlorosaccharides, and 65% were sucralose
<1000 ppm DMF
13% NaCl
2% Organic salts including DMAHCl, and
80% water.

This solution was concentrated to about 34% carbohydrates via removal of about 70% of weight by evaporation under vacuum. Filtration of the salt produced a resultant stream that was assayed to contain 15% DMA by weight and 2.3% sodium by weight. This was subsequently diluted 1:4 with water to obtain reasonable viscosity. This stream was charged to a column of DOW HCRS resin which had been washed with either 10% NaCl or 5% NaOH. When charged with 3 equivalents of DMA per liter of resin, about 78% of charged DMA was retained on the resin. 100% of charged DMA was retained when charged with only 1 equivalent DMA per liter of packed resin. 92% of charged DMA was retained when charged with 2 equivalents DMA per liter of packed resin. Some dilution was experienced as residual sucralose was displaced prior to resin regeneration.

EXAMPLE 2

Experimental Demonstration of the Effect of NaCl and DMAHCL on Partition Coefficient A series of aqueous solutions containing DMAHCl, NaCl and sucralose were made up in water as shown in Table 1. The solutions were all clear and colorless at room temperature.

TABLE 1

| | Gms Wt | | | | | |
|---|---|---|---|---|---|---|
| Exp | DMAHCL | NaCl | Sucralose | Water | DS/g | total wt |
| #3 | 0.030 | 0.82 | 2.300 | 8.34 | 3.15 | 11.49 |
| #4 | 0.034 | 0.18 | 2.257 | 8.34 | 2.47 | 10.81 |
| #5 | 0.390 | 0.75 | 2.100 | 7.69 | 3.24 | 10.93 |
| #8 | 0.416 | 0.17 | 2.250 | 8.33 | 2.84 | 11.17 |
| #9 | 0.213 | 0.43 | 1.167 | 8.35 | 1.81 | 10.16 |

Each sample was shaken with about 37 g of ethyl acetate (EA). The mixture was allowed to settle, resulting in the formation of a heavy phase (aqueous) and a light phase (EA based). The weights of these respective phases were recorded and each phase was analysed for its sucralose content. The dry solids content of each phase was also measured by evaporation to dryness (moisture balance). The results are given below in Table 2.

TABLE 2

Mass and analysis of the lower ("heavy") phase

| | Heavy phase | | | | | |
|---|---|---|---|---|---|---|
| | Total Wt/g | DS | Dry solids | Wt % sucralose HPLC | Wt sucralose/g | Wt % heavy |
| #3 | 9.56 | 13.31 | 1.27 | 29.88 | 0.380 | 3.98% |
| #4 | 9.1 | 7.94 | 0.72 | 67.59 | 0.488 | 5.37% |
| #5 | 9.41 | 17.26 | 1.62 | 25.49 | 0.414 | 4.40% |
| #8 | 9.7 | 12.04 | 1.17 | 47.68 | 0.557 | 5.74% |
| #9 | 9.7513 | 10.45 | 1.02 | 33.73 | 0.344 | 3.52% |

TABLE 3

Mass and analysis of the upper ("light") phase

| | Light phase | | | | | |
|---|---|---|---|---|---|---|
| Exp | Wt/g light | DS | Dry Solids/g | Wt % sucralose HPLC | Wt sucralose/g | Wt % Light |
| #3 | 40.780 | 5.59 | 2.28 | 98.2 | 2.238 | 5.49% |
| #4 | 37.970 | 5.30 | 2.01 | 94.23 | 1.896 | 4.99% |
| #5 | 38.370 | 5.03 | 1.93 | 95.59 | 1.843 | 4.80% |
| #8 | 39.010 | 4.77 | 1.86 | 99.47 | 1.853 | 4.75% |
| #9 | 34.677 | 3.12 | 1.08 | 85.33 | 0.923 | 2.66% |

From the data presented, it is possible to calculate the distribution coefficient K for each experiment, where K is defined as:

$$K = (\text{Wt \% Sucralose in light phase})/(\text{Wt \% sucralose in heavy phase})$$

TABLE 4

| Exp | Calculated K |
|---|---|
| #3 | 1.38 |
| #4 | 0.93 |
| #5 | 1.09 |
| #8 | 0.83 |
| #9 | 0.76 |

Statistical Analysis

The above experimental data may be summarized as shown in Table 5, where the weights of DMAHCl, NaCl and sucralose have been expressed as wt % on water in the initial feed to the experiment:

TABLE 5

| Exp | DMAHCL | NaCl | Sucralose | Actual K |
|---|---|---|---|---|
| #3 | 0.36% | 9.87% | 27.58% | 1.38 |
| #4 | 0.41% | 2.10% | 27.06% | 0.93 |
| #5 | 5.07% | 9.75% | 27.31% | 1.09 |
| #8 | 4.99% | 2.04% | 27.01% | 0.83 |
| #9 | 2.55% | 5.15% | 13.98% | 0.76 |

Statistical analysis of this data using multiple regression techniques shows that the concentrations of all these components influence the observed K value:

TABLE 6

Regression coefficients from multiple regression analysis

| | Coefficients |
|---|---|
| Intercept | 0.337406 |
| DMAHCL % | −4.07637 |
| NaCl % | 4.516977 |
| Sucralose % | 2.063842 |

Table 6 shows that the weight % concentrations of sodium chloride and sucralose have a positive effect on K (i.e.: the more there is of these components in the feed the higher the K value) whereas surprisingly, the weight % of DMAHCl has the opposite effect—the higher the weight % of DMAHCl, the lower K is. If these regression coefficients are used to predict the K values, a close correlation is seen, as shown in Table 7:

TABLE 7

Actual K vs. predicted K (Pred K)

| Exp | Actual K | Pred K |
|---|---|---|
| #3 | 1.38 | 1.34 |
| #4 | 0.93 | 0.97 |
| #5 | 1.09 | 1.13 |
| #8 | 0.83 | 0.78 |
| #9 | 0.76 | 0.75 |

Discussion

It is apparent from this data that sodium chloride exhibits the classic "salting out" effect. This effect is usually explained by saying that the dissolution of the NaCl in the aqueous phase results in a highly polar medium (due to the ion pairs). In this medium, the solvation energy for electrically neutral carbohydrate based species (such as sucralose) will be relatively low and thus the sucralose will partition preferentially into the ethyl acetate phase (hence a relatively high K).

DMAHCl is also a salt and may have been expected to show a similar effect to NaCl. However, surprisingly it shows the opposite effect. The reason for this is not clear.

Conclusion: Consequences for the Process

Figure 1:
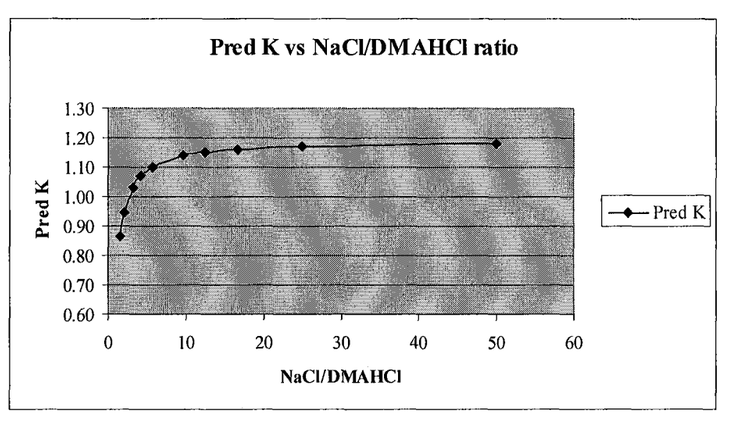
FIG. 1 shows the effect of the ratio of NaCl to DMAHCl (all other parameters being kept constant) on the predicted distribution coefficient (Pred K).

The accompanying drawing shows the effect of the ratio of NaCl to DMAHCl (all other parameters being kept constant) on the predicted distribution coefficient (Pred K).

The invention claimed is:

1. A process for the extraction of sucralose or a sucralose-6-acylate from an aqueous solution containing at least said sucralose or said sucralose-6-acylate, other chlorinated saccharides, dimethylammonium chloride, and a further chloride selected from the group consisting of alkali metal chlorides, ammonium chloride and alkaline earth metal chlorides, into an organic solvent for said sucralose or said sucralose-6-acylate by contacting said organic solvent with said solution to extract said sucralose or said sucralose-6-acylate into the organic solvent, in which the ratio of said further chloride to dimethylammonium chloride in said aqueous solution is increased prior to or during said contact so as to increase the partition coefficient of said sucralose or said sucralose-6-acylate into said organic solvent;
wherein dimethylammonium chloride is removed from the aqueous solution prior to said extraction to increase the ratio of said further chloride to dimethylammonium chloride.

2. A process for the extraction of sucralose or sucralose-6-acylate from an aqueous solution containing at least said sucralose or said sucralose-6-acylate, other chlorinated saccharides, dimethylammonium chloride, and a further chloride selected from the group consisting of alkali metal chlorides, ammonium chloride and alkaline earth metal chlorides, into an organic solvent for said sucralose or said sucralose-6-acylate, which comprises the steps:
removing dimethylammonium chloride from the aqueous solution to increase the ratio of said further chloride to dimethylammonium chloride and thus increase the partition coefficient of sucralose into said organic solvent; and
contacting said organic solvent with the resulting solution to extract said sucralose or said sucralose-6-acylate into the organic solvent.

3. A process for the purification of sucralose from a feed stream from the synthesis of sucralose, in which the feed stream is subjected to a series of purification steps, at least one of the steps comprising: extracting sucralose from an aqueous solution containing at least sucralose, other chlorinated saccharides, dimethylammonium chloride, and a further chloride selected from the group consisting of alkali metal chlorides, ammonium chloride and alkaline earth metal chlorides, into an organic solvent for sucralose by contacting said organic solvent with said solution to extract sucralose into the organic solvent, in which the ratio of said further chloride to dimethylammonium chloride in said aqueous solution is increased prior to or during said contact so as to increase the partition coefficient of sucralose into said organic solvent;
wherein dimethylammonium chloride is removed from the aqueous solution prior to said extraction to increase the ratio of said further chloride to dimethylammonium chloride.

4. A process for the production of sucralose from a feed stream from the synthesis of sucralose-6-acylate, in which the feed stream is subjected to a series of purification steps and the purified sucralose-6-acylate is then deacylated to give sucralose, at least one of the purification steps comprising: extracting sucralose-6-acylate from an aqueous solution containing at least sucralose-6-acylate, other chlorinated saccharides, dimethylammonium chloride, and a further chloride selected from the group consisting of alkali metal chlorides, ammonium chloride and alkaline earth metal chlorides, into an organic solvent for sucralose-6-acylate by contacting said organic solvent with said solution to extract sucralose-6-acylate into the organic solvent, in which the ratio of said further chloride to dimethylammonium chloride in said aqueous solution is increased prior to or during said contact so as to increase the partition coefficient of sucralose-6-acylate into said organic solvent;
wherein dimethylammonium chloride is removed from the aqueous solution prior to said extraction to increase the ratio of said further chloride to dimethylammonium chloride.

5. The process of claim 2, wherein the dimethylammonium chloride is removed by pH adjustment to form free dimethylamine, and evaporation of the dimethylamine by application of heat and/or vacuum.

6. The process of claim 1, wherein the dimethylammonium chloride is removed by pH adjustment to form free dimethylamine, and evaporation of the dimethylamine by application of heat and/or vacuum.

7. The process of claim 3, wherein the dimethylammonium chloride is removed by pH adjustment to form free dimethylamine, and evaporation of the dimethylamine by application of heat and/or vacuum.

8. The process of claim 4, wherein the dimethylammonium chloride is removed by pH adjustment to form free dimethylamine, and evaporation of the dimethylamine by application of heat and/or vacuum.

9. The process of claim 2, wherein sufficient dimethylammonium chloride is removed to reduce its concentration in the aqueous solution to no more than 20,000 ppm.

10. The process of claim 1, wherein sufficient dimethylammonium chloride is removed to reduce its concentration in the aqueous solution to no more than 20,000 ppm.

11. The process of claim 3, wherein sufficient dimethylammonium chloride is removed to reduce its concentration in the aqueous solution to no more than 20,000 ppm.

12. The process of claim 4, wherein sufficient dimethylammonium chloride is removed to reduce its concentration in the aqueous solution to no more than 20,000 ppm.

13. The process of claim 9, wherein sufficient dimethylammonium chloride is removed to reduce its concentration in the aqueous solution to no more than 1,000 ppm.

14. The process of claim 10, wherein sufficient dimethylammonium chloride is removed to reduce its concentration in the aqueous solution to no more than 1,000 ppm.

15. The process of claim 11, wherein sufficient dimethylammonium chloride is removed to reduce its concentration in the aqueous solution to no more than 1,000 ppm.

16. The process of claim 12, wherein sufficient dimethylammonium chloride is removed to reduce its concentration in the aqueous solution to no more than 1,000 ppm.

17. The process of claim 1, wherein the ratio of said further chloride to dimethylammonium chloride in said aqueous solution is increased to a value of from 10:1 to 100:1.

18. The process of claim 2, wherein the ratio of said further chloride to dimethylammonium chloride in said aqueous solution is increased to a value of from 10:1 to 100:1.

19. The process of claim 3, wherein the ratio of said further chloride to dimethylammonium chloride in said aqueous solution is increased to a value of from 10:1 to 100:1.

20. The process of claim 4, wherein the ratio of said further chloride to dimethylammonium chloride in said aqueous solution is increased to a value of from 10:1 to 100:1.

21. The process of claim 1, wherein the ratio of said further chloride to dimethylammonium chloride in said aqueous solution is increased to a value of from 10:1 to 25:1.

22. The process of claim 2, wherein the ratio of said further chloride to dimethylammonium chloride in said aqueous solution is increased to a value of from 10:1 to 25:1.

23. The process of claim 3, wherein the ratio of said further chloride to dimethylammonium chloride in said aqueous solution is increased to a value of from 10:1 to 25:1.

24. The process of claim 4, wherein the ratio of said further chloride to dimethylammonium chloride in said aqueous solution is increased to a value of from 10:1 to 25:1.

25. The process of claim 1, in which, prior to the extraction, the aqueous solution is evaporated to increase the dry solids content to a level of from 15% to 65%.

26. The process of claim 2, in which, prior to the extraction, the aqueous solution is evaporated to increase the dry solids content to a level of from 15% to 65%.

27. The process of claim 3, in which, prior to the extraction, the aqueous solution is evaporated to increase the dry solids content to a level of from 15% to 65%.

28. The process of claim 4, in which, prior to the extraction, the aqueous solution is evaporated to increase the dry solids content to a level of from 15% to 65%.

29. The process of claim 25, wherein the dry solids content is increased to a level of from 30% to 55%.

30. The process of claim 26, wherein the dry solids content is increased to a level of from 30% to 55%.

31. The process of claim 27, wherein the dry solids content is increased to a level of from 30% to 55%.

32. The process of claim 28, wherein the dry solids content is increased to a level of from 30% to 55%.

33. The process of claim 1, wherein said further chloride is sodium chloride.

34. The process of claim 2, wherein said further chloride is sodium chloride.

35. The process of claim 3, wherein said further chloride is sodium chloride.

36. The process of claim 4, wherein said further chloride is sodium chloride.

37. The process of claim 1, wherein said organic solvent comprises a solvent selected from the group consisting of methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, n-butanol, and mixtures thereof.

38. The process of claim 2, wherein said organic solvent comprises a solvent selected from the group consisting of methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, n-butanol, and mixtures thereof.

39. The process of claim 3, wherein said organic solvent comprises a solvent selected from the group consisting of methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, n-butanol, and mixtures thereof.

40. The process of claim 4, wherein said organic solvent comprises a solvent selected from the group consisting of methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, n-butanol, and mixtures thereof.

41. The process of claim 37, wherein the solvent is ethyl acetate.

42. The process of claim 38, wherein the solvent is ethyl acetate.

43. The process of claim 39, wherein the solvent is ethyl acetate.

44. The process of claim 40, wherein the solvent is ethyl acetate.

45. The process of claim 1, wherein the volume ratio of said organic solvent to said aqueous solution is from 2:1 to 5:1.

46. The process of claim 2, wherein the volume ratio of said organic solvent to said aqueous solution is from 2:1 to 5:1.

47. The process of claim 3, wherein the volume ratio of said organic solvent to said aqueous solution is from 2:1 to 5:1.

48. The process of claim 4, wherein the volume ratio of said organic solvent to said aqueous solution is from 2:1 to 5:1.

49. The process of claim 45, wherein the volume ratio of said organic solvent to said aqueous solution is from 3:1 to 4:1.

50. The process of claim 46, wherein the volume ratio of said organic solvent to said aqueous solution is from 3:1 to 4:1.

51. The process of claim 47, wherein the volume ratio of said organic solvent to said aqueous solution is from 3:1 to 4:1.

52. The process of claim 48, wherein the volume ratio of said organic solvent to said aqueous solution is from 3:1 to 4:1.

53. The process of claim 37, wherein said organic solvent comprises a solvent selected from the group consisting of ethyl acetate, iso-propyl acetate, n-propyl acetate, n-butyl acetate, methyl iso-butyl ketone, n-butanol, and mixtures thereof.

54. The process of claim 38, wherein said organic solvent comprises a solvent selected from the group consisting of ethyl acetate, iso-propyl acetate, n-propyl acetate, n-butyl acetate, methyl iso-butyl ketone, n-butanol, and mixtures thereof.

55. The process of claim 39, wherein said organic solvent comprises a solvent selected from the group consisting of ethyl acetate, iso-propyl acetate, n-propyl acetate, n-butyl acetate, methyl iso-butyl ketone, n-butanol, and mixtures thereof.

56. The process of claim 40, wherein said organic solvent comprises a solvent selected from the group consisting of ethyl acetate, iso-propyl acetate, n-propyl acetate, n-butyl acetate, methyl iso-butyl ketone, n-butanol, and mixtures thereof.

* * * * *